(12) United States Patent
  Battista

(10) Patent No.:  US 12,642,478 B2
(45) Date of Patent:  Jun. 2, 2026

(54) SYSTEM AND METHOD FOR DETERMINING MOTOR SIGNS OF NEURODEGENERATIVE DISORDERS

(71) Applicant: Biomedical Lab S.r.l., Potenza (IT)

(72) Inventor: Luigi Battista, Potenza (IT)

( * ) Notice: Subject to any disclaimer, the term of this patent is extended or adjusted under 35 U.S.C. 154(b) by 226 days.

(21) Appl. No.: 18/543,870

(22) Filed: Dec. 18, 2023

(65) Prior Publication Data

US 2025/0194988 A1    Jun. 19, 2025

(51) Int. Cl.
  *A61B 5/00* (2006.01)
  *A61B 5/11* (2006.01)

(52) U.S. Cl.
  CPC .......... *A61B 5/4082* (2013.01); *A61B 5/1101* (2013.01); *A61B 5/1116* (2013.01); *A61B 5/1118* (2013.01); *A61B 5/681* (2013.01); *A61B 5/7257* (2013.01); *A61B 5/7282* (2013.01); *A61B 2562/0219* (2013.01)

(58) Field of Classification Search
  CPC ... A61B 5/4082; A61B 5/1101; A61B 5/1116; A61B 5/1118; A61B 5/681; A61B 5/7257; A61B 5/7282; A61B 2562/0219; A61B 5/7246; G16H 50/20
  See application file for complete search history.

(56) References Cited

U.S. PATENT DOCUMENTS

| | | | |
|---|---|---|---|
| 2012/0245481 A1* | 9/2012 | Blanco ................ | A61B 5/4094 |
| | | | 600/544 |
| 2015/0309563 A1* | 10/2015 | Connor ............... | A61B 5/1071 |
| | | | 73/865.4 |
| 2021/0128024 A1* | 5/2021 | Battista ............... | A61B 5/4082 |
| 2022/0350398 A1* | 11/2022 | Spinelli .................. | G06F 3/011 |

OTHER PUBLICATIONS

Postuma R. et al. MDS Clinical Diagnostic Criteria for Parkinson's Disease, Published online in Wiley Online Library (wileyonlinelibrary.com). DOI: 10.1002/mds.26424, Accepted Aug. 9, 2015.
Schalkamp a. et al., Wearable movement-tracking data identify Parkinson's disease years before clinical diagnosis, Nature Medicine, 2023-07-03.
Cova, I. et al., Diagnostic biomarkers for Parkinson's disease at a glance: where are we?, Journal of Neural Transmission (2018) 125:1417-1432, 2018-08-25.

(Continued)

*Primary Examiner* — Jacqueline Cheng
*Assistant Examiner* — Tho Q Tran
(74) *Attorney, Agent, or Firm* — Themis Law

(57) ABSTRACT

A system and related method for determining a motor state of a subject includes a multi-axial measurement system and a processor that measure a signal indicative of an acceleration trend on three axes, limiting the frequency band and compensating the offset of the output signals from the multi-axial measurement system; compute a motor activity; perform a frequency and spectral analysis of the signal with the Fournier transform; computing the power spectral density; compute integrals of the power spectral density calculated by considering a pre-determined frequency interval and the entire frequency range; and compare the determined parameters against a reference value or range.

19 Claims, 10 Drawing Sheets

(56)     References Cited

OTHER PUBLICATIONS

He, R., Recent Advances in Biomarkers for Parkinson's Disease, Frontiers in Aging Neuroscience (2018), vol. 10, Article 305, Oct. 11, 2018.

Kim, D. et al., A Comparison of Activity Monitor Data from Devices Worn on the Wrist and the Waist in People with Parkinson's Disease, Movement Disorders Clinical Practice 2019; 6(8): 693-699. doi: 10.1002/mdc3.12850.

Jankovic, J., Parkinson's disease: clinical features and diagnosis, J Neurol Neurosurg Psychiatry 2008;79:368-376. doi:10.1136/jnnp. 2007.131045.

Hiung, F. et al., Development of wrist monitoring device to measure wrist range of motion, IOP Conf. Series: Materials Science and Engineering 788 (2020) 012033, IOP Publishing, doi: 10.1088/1757-899X/788/1/012033.

Otten, P. et al., A Framework to Automate Assessment of Upper-Limb Motor Function Impairment: A Feasibility Study, Sensors 2015, 15, 20097-20114; doi:10.3390/s150820097, Aug. 14, 2015.

Abyarjoo, F. et al., Monitoring Human Wrist Rotation in Three Degrees of Freedom, IEEE, 978-1-4799-0053-4/13 (2013).

Berg, D. et al., MDS Research Criteria for Prodromal Parkinson's Disease, Movement Disorders, vol. 30, No. 12 (2015).

* cited by examiner

A) HAND MOVEMENTS

B) PRONATION-SUPINATION

A) POSTURAL TREMOR

B) REST TREMOR AMPLITUDE 3.17

A) PRONATION-SUPINATION

B) REST TREMOR AMPLITUDE

SYSTEM AND METHOD FOR DETERMINING MOTOR SIGNS OF NEURODEGENERATIVE DISORDERS

FIELD OF THE INVENTION

The present industrial invention refers to an apparatus and a method for the determination of motor signs due to Parkinson's disease, Parkinsonism, and neurodegenerative disorders.

More specifically, the invention concerns a device and a method, which enable the determination of motor signs related to Parkinson's disease and Parkinsonism by accurately distinguishing motor manifestations of such diseases from regular activities performed daily by a healthy subject.

BACKGROUND OF THE INVENTION

Parkinson's disease (PD) is the second most common neurodegenerative disorder, with an estimated 10 million people worldwide living with this affliction; PD typically develops between the ages of 55 and 65 years and occurs in 1%-2% of people over the age of 60, rising to 3.5% at age 85-89 years.

According to Movement Disorder Society (MDS) Clinical Diagnostic Criteria for PD, until definitive and validated diagnostic markers are available, clinical expert opinion will be the gold standard diagnostic technique during life. The PD diagnosis is based on a two-step process: first, Parkinsonism is defined, as bradykinesia in combination with either rest tremor, rigidity, or both; then, after Parkinsonism is diagnosed, the criteria then define whether this Parkinsonism is attributable to PD according to predetermined criteria (POSTUMA ET AL., MDS clinical diagnostic criteria for Parkinson's disease. Mov Disord. 2015 October; 30 (12): 1591-601. doi: 10.1002/mds.26424).

For the first step, the MDS Criteria define that examination of all cardinal manifestations (i.e. bradykinesia, in combination with either rest tremor, rigidity, or both) should be carried out as described in the Motor Examination section (Part 3) of the Unified Parkinson's Disease Rating Scale (MDS-UPDRS), taking into account that although the MDS-UPDRS rates PD, it does not define it and, therefore, no single cutoff score on the MDS-UPDRS items should be used to define Parkinsonism.

Nowadays, some aspects of the clinical diagnosis of PD are often judged unsatisfactory, because the diagnostic process is considered to largely rely on clinical criteria, with the consequence that it is very difficult to formulate an early PD diagnosis, as well as an accurate and timely differential diagnosis between PD and other Parkinsonisms. Moreover, other widely reported shortcomings are represented by time-limited duration of the above-mentioned clinical examinations that may typically fail to capture daily fluctuations in motor signs, by the presence of subjective aspects in the clinical ratings and by the circumstance that patients self-reporting is not always reliable.

In order to reduce these drawbacks, a great effort in searching reliable markers/biomarkers and tools both for early diagnosis and prognosis in PD is currently ongoing. Proposed biomarkers include clinical, imaging, biofluidic-base, inflammation-related biomarkers for preclinical, prodromal and clinical stage (e.g. U.S. Pat. No. 9,927,445 B2; US20170335395A1; U.S. Pat. No. 11,499,971 B2); some of the proposed tools and methods for the early detection of PD are based on analyzing voice disorders (U.S. Pat. No. 9,198,613 B2), handwriting (CN 115346661 A), olfactory testing (RU2478209 C1) and accelerometry data (US20170007168 A1; SCHALKAMP ET AL., Wearable movement-tracking data identify Parkinson's disease years before clinical diagnosis. Nat Med. 2023 Jul. 3. doi: 10.1038/s41591-023-02440-2).

However, there are currently no means to identify prodromal PD with 100% certainty, neither standardized international criteria supporting PD diagnosis at a preclinical stage, nor confirmed biomarkers to provide early detection of PD efficiently (COVA ET AL., Diagnostic biomarkers for Parkinson's disease at a glance: where are we? J Neural Transm. 2018 October; 125 (10): 1417-1432. doi: 10.1007/s00702-018-1910-4); on the other hand, an increasing number of studies have revealed that a combination of biomarkers can improve the diagnostic accuracy of individual biomarkers (HE ET AL., Recent Advances in Biomarkers for Parkinson's Disease. Front Aging Neurosci. 2018 Oct. 11; 10:305. doi: 10.3389/fnagi.2018.00305).

Digital biomarkers, smartphones and smartwatches could provide objective, sensitive, real-world measures of PD; indeed, several technology-based objective measures (TOMs) have already been proposed, both for the assessment of motor signs due to PD and for the extraction of key features in order to differentiate individuals with early PD from healthy controls.

In a recent study, a wrist-worn accelerometer was used to detect motor activity during a period of seven days finding that accelerometry data predicts prodromal PD, since daily average acceleration in healthy subjects is greater than one in PD patients and acceleration is reduced several years before PD diagnosis (SCHALKAMP ET AL., Wearable movement-tracking data identify Parkinson's disease years before clinical diagnosis. Nat Med. 2023 Jul. 3. doi: 10.1038/s41591-023-02440-2).

However, another study found that wrist monitors are likely to overestimate steps and activity, particularly in people with tremor and dyskinesia, and this is probably due to the result of these impairments leading to increased upper limb movements, which are erroneously recorded as steps and activity counts by the activity monitor (KIM ET AL., A Comparison of Activity Monitor Data from Devices Worn on the Wrist and the Waist in People with Parkinson's Disease. Mov Disord Clin Pract. 2019 Oct. 18; 6(8):693-699. doi: 10.1002/mdc3.12850). As a consequence, evaluating only the acceleration or motor activity of data measured by sensors could be not enough to reasonably distinguish healthy people from PD patients with mild to moderate tremor due to the concurrence of two opposite effects, the acceleration reduction due to PD and possible overestimation of activity due to tremor.

Presently, the currently available tests could confuse movements that are not due to movement disorders with movements due to Parkinsonism, which creates results that are not entirely accurate.

SUMMARY OF THE INVENTION

The objective of the present invention is therefore to provide an innovative device, and a related method, which solves the above-mentioned technical problems.

More specifically, an objective of the present invention is to provide a device, and a related method, to carry out the recording of the movements and accurately distinguish normal movements from those due to a Parkinson's disease and Parkinsonism. These and other objectives are therefore obtained with the present device to determine the motor state of the subject as disclosed herein.

A system according to the invention is structured to determine the motor state of a subject and in one embodiment includes a wearable device, a sensor arranged in the wearable device that is provided with a multi-axial measuring system for detecting a signal indicative of a motion of a limb or other body parts of the subject, a signal converter that converts the signal into data, a storage unit that receives and stores the data detected by the multi-axial measurement system, a processor that processes and re-arranges the data stored in the memory, and a user interface that interacts with the processor and displays final results derived from the computed parameters using textual and/or graphical elements.

The multi-axial measuring system may be configured as a tri-axial accelerometer, and the wearable device may be configured to be worn on the wrist of the subject. An external processing unit may be in communication with the wearable device and, in one embodiment, house the processor.

The processor is programmed to process the data by subdividing a recording sequence, during which the signal is collected, into time sub-intervals; by computing parameters for each sub-interval; and by comparing those parameters against a reference value or range to verify whether the determined motor state matches a reference motor state to a predetermined degree.

The parameters computed by the processor may include:
- a Fourier transform at each axis of the multi-axial measurement system, with a spectral processing for determining a frequency content of the signal at each axis of the multi-axial measurement system;
- a motor activity parameter and a first integral of the power spectral density calculated by considering an entire frequency range;
- a second integral of the power spectral density calculated by considering a pre-determined frequency interval, and
- a ratio between the second integral and the first integral, such the ratio being adjusted to take into account whether, within each time sub-interval, a pronation-supination movement is determined, and whether the pronation-supination movement from the motion of the limb or of the plurality of parts matches a pronation-supination reference pattern to a predetermined degree.

The processor then processes the parameters determined for each time sub-interval and computes an average value of the motor activity parameter by considering multiple time sub-intervals and an average value of the adjusted ratios between the second integral and the first integral over the multiple time sub-intervals.

More particularly, the determined motor state is found to match the reference motor state when:

$$\begin{cases} a_{RMS} < a_T \\ BL > BL_T \end{cases}$$

wherein:
$a_T$ and $BL_T$ are thresholds,
$a_{RMS}$ is an average value of the root mean square acceleration values determined for each time sub-interval of the recording sequence,
BL is an average value of the ratio values determined for each time sub-interval of the recording sequence, where such the ratio is between two integrals: (a) the second integral of the power spectral density calculated on the pre-determined frequency interval which is greater than zero for the time sub-intervals where the pronation-supination movement is determined, the second integral being equal to zero for the time sub-intervals where the pronation-supination movement is not determined, and (b) the first integral of the power spectral density calculated over an entire frequency range.

In one embodiment, the processor is programmed to identify the motor state associated with Parkinson's disease tremor by considering the power spectral density and the frequency values within intervals between 3 and 7 Hz.

The processor may be programmed to carry out a recording session continuously over a predetermined amount of time and actively, with an active involvement of the subject in pre-determined motor tasks; or continuously over a pre-determined amount of time and passively, without involvement by the subject in pre-determined motor tasks; or the recording sequence may take place both passively and actively, with an active involvement of the subject in the pre-determined motor tasks. The processor may also be programmed to carry out a recording session over a single sub-interval.

The processor may also be programmed to perform, during an active recording sequence in which the subject is actively involved in pre-determined motor tasks:
- a computation of acceleration signals detected by the sensor to determine the average value of the root mean square acceleration values determined during the active recording sequence,
- the spectral processing of the acceleration signals and a computation of the Fourier transform at each axis of the multi-axial measurement system, the spectral processing determining the frequency content of the acceleration signals at each axis of the multi-axial measurement system, to determine one or more of:
- frequency peaks occurring in a specific frequency range, or
- one or more of the parameters related to Fourier transforms, and
- a comparison of one or more of the frequency peaks or of the preceding parameters against reference values or ranges, to verify whether the determined motor state matches the reference motor state to a predetermined degree.

Further, the processor may be programmed to receive signals detected during the execution of motor tests performed with the subject's hands and determine the motor state based on rest tremor amplitude and the pronation-supination movements of the hands, and to verify whether the determined motor state matches the reference motor state if:

$$\begin{cases} a_{RMS} < a_{T,B} \\ f_{P,z} < f_{P,B} \end{cases}$$

during the recording session of the pronation-supination movements, and $$\begin{cases} a_{RMS} > a_{T,T} \\ f_{P,TL} \le f_{P,y} \le f_{P,TH} \end{cases}$$

during the recording session of the rest tremor amplitude, wherein:
$a_{T,T}$ and $a_{T,B}$ are thresholds,

5

$f_{P,B}$, $f_{P,TL}$ and $f_{P,TH}$ are frequency values, $f_{P,z}$ is a frequency value in which a peak of the Fourier transform of an acceleration signal at a z-axis occurs during the recording session of the pronation-supination movements, $f_{P,y}$ is a frequency value in which the peak of the Fourier transform of an acceleration signal at a y-axis occurs during the recording session of the rest tremor amplitude.

Still further, the processor may be programmed to perform a supplemental processing and comparison of parameters determined both during a recording session passively and actively to verify whether the determined motor state matches the reference motor state to a predetermined degree.

Yet further, the processor may be programmed to confirm the results obtained passively during the recording sessions with results obtained actively during the recording session.

A system according to the invention, as described herein, may therefore be used to precisely determine any motor signs due to neurodegenerative diseases.

BRIEF DESCRIPTION OF THE DRAWINGS

Features and advantages of a device and of the related measurement method according to the invention will be made clearer with the following description of some features, which are provided as non-limiting examples, together with the enclosed drawings, in which:

FIG. 5 further shows the set of real tests together with a schematic representation of the achievable performances.

6

Figure 8:
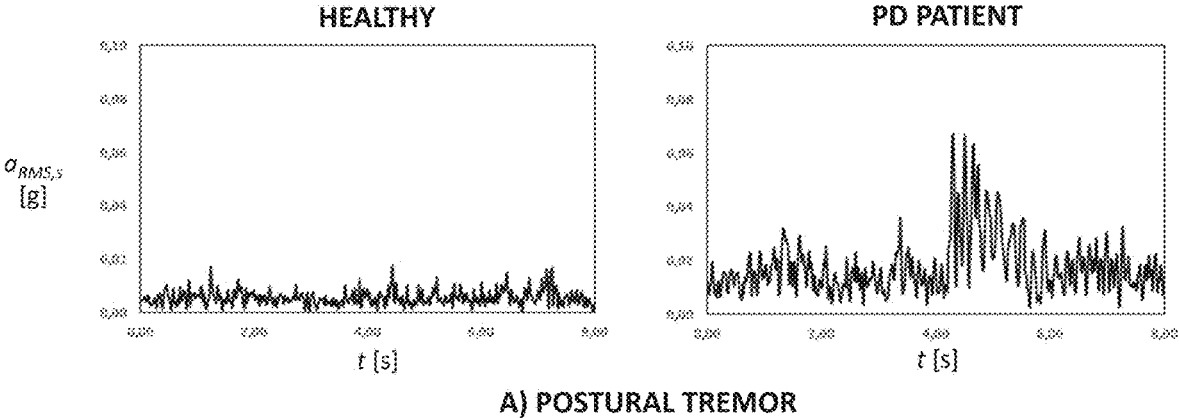
Figure 8:
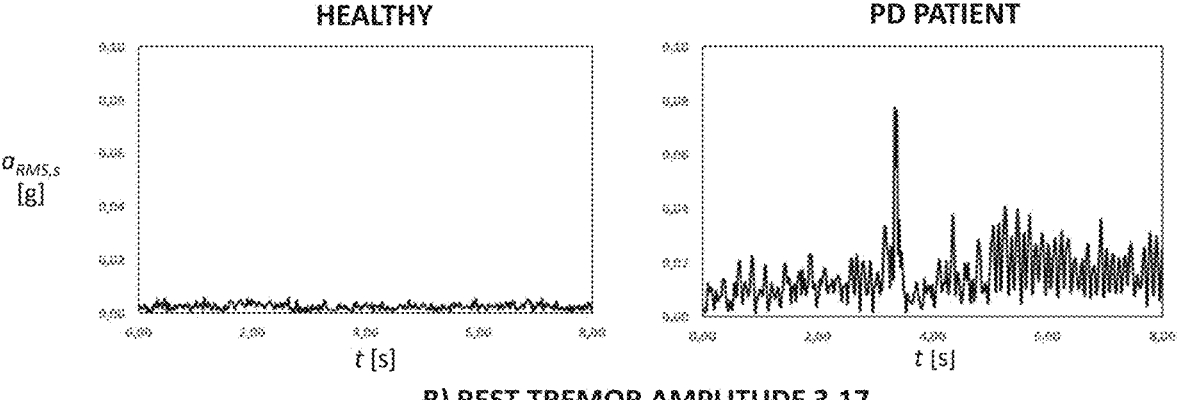

FIG. 8 shows an example of the temporal patterns of $a_{RMS,s}$ determined during the execution of motor tests on postural tremor (A) and rest tremor amplitude (B) in a normal subject (left column) and in a subject with PD (right column).

Figure 9:
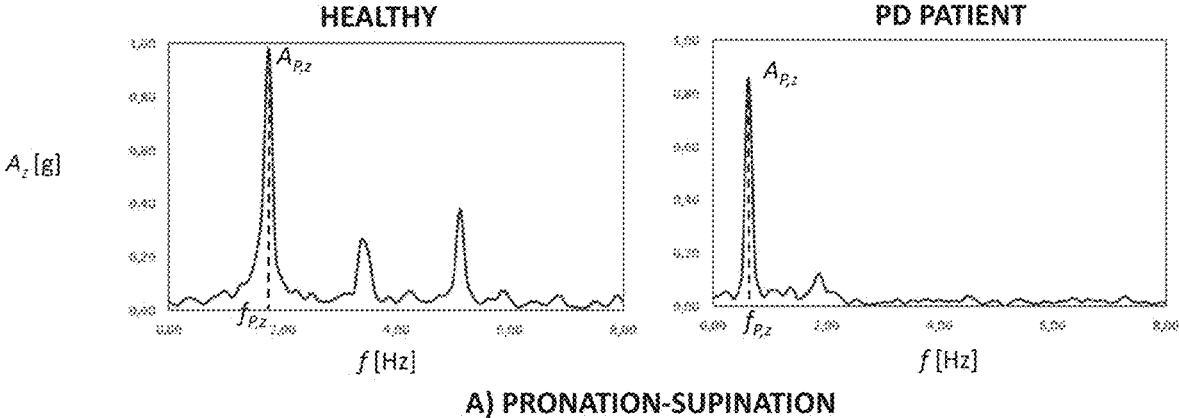
Figure 9:
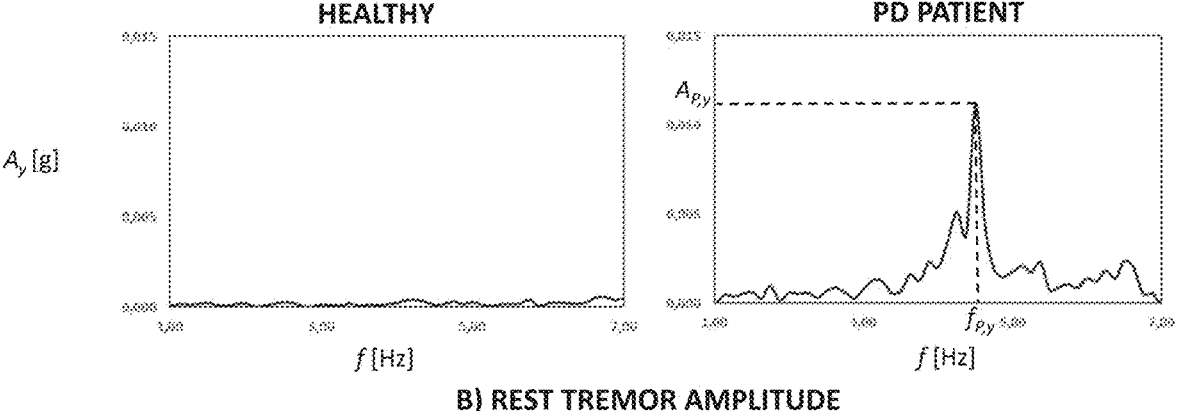

FIG. 9 shows an example of the Fast Fourier Transform determined during the execution of motor tests on pronation-supination movements (A) and rest tremor amplitude (B) in a normal subject (left column) and in a subject with PD (right column).

The measurements, information, and data disclosed herein are from procedures carried out in accordance with the Helsinki Declaration, and consequently, the informed consent of the volunteers involved in the studies that led to the invention had been previously acquired.

DETAILED DESCRIPTION OF EMBODIMENTS OF THE INVENTION

Detailed descriptions of embodiments of the invention are provided herein. It is to be understood, however, that the present invention may be embodied in various forms. Therefore, the specific details disclosed herein are not to be interpreted as limiting, but rather as a representative basis for teaching one skilled in the art how to employ the present invention in virtually any detailed system, structure, or manner.

In one aspect, a system according to the invention can not only measure whether the motion of a subject (for example, the motion of one or both hands) differs from a motioned considered to be normal for that subject, but can also detect whether the motion of a patient includes parameters that are associated with the tremor observed with Parkinson's disease or Parkinsonism.

Figure 1:
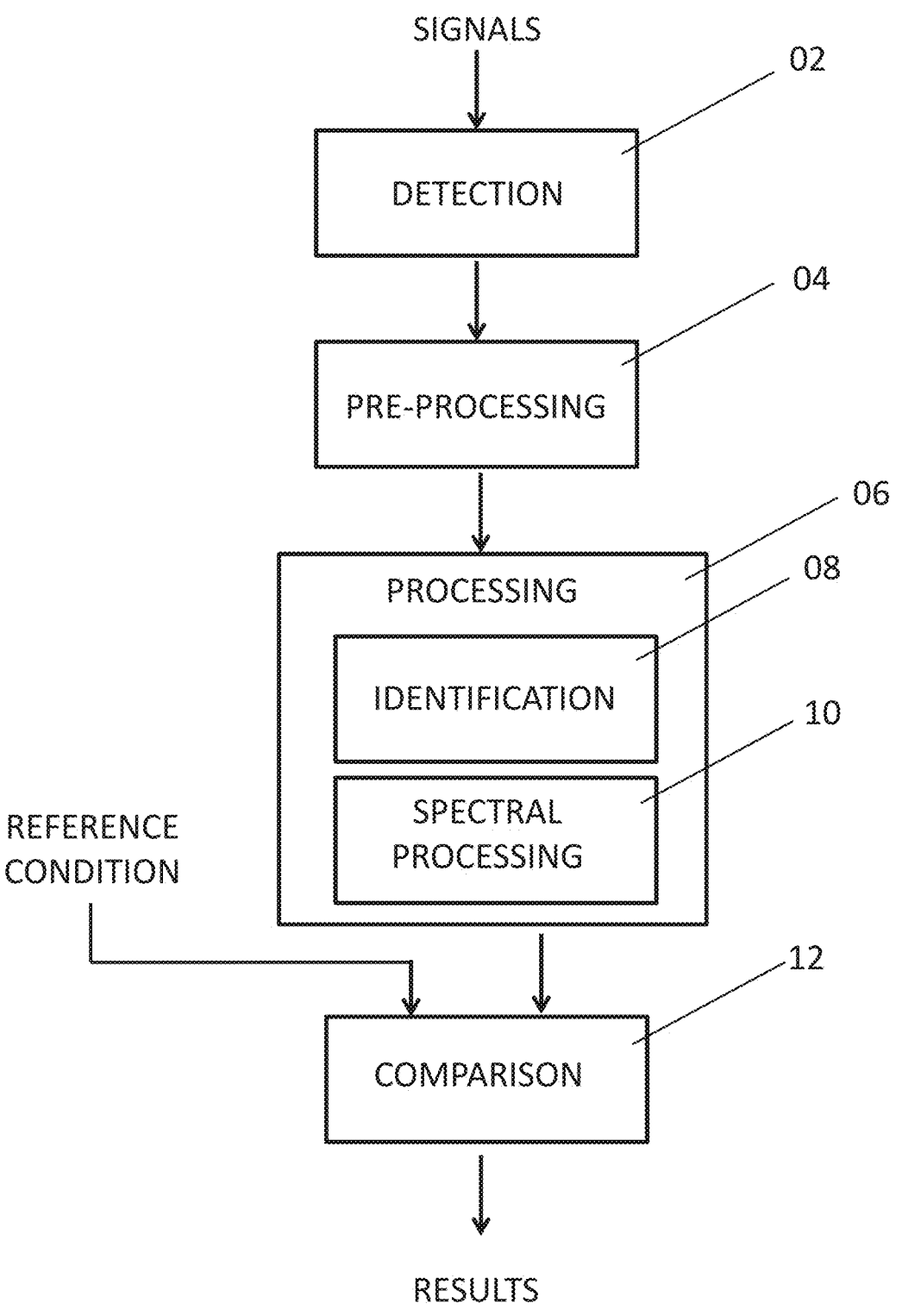
FIG. 1 schematically illustrates the main steps of the identification method, quantitative evaluation and comparison of the parameters, according to which a device according to the invention operates.

FIG. 1 depicts a flowchart that shows the steps for determining a movement, and therefore the kinetic state, of a patient.

More specifically, a device according to the invention can identify a motor state and evaluate the presence of possible movement disorders in a number of steps, which include the following:

Detecting 02 signals containing information regarding the movement of body limbs and other parts of the patient's body;

Pre-processing 04 such signals to limit the frequency band, reduce artifacts, and compensate for the offset of the output signals from the multi-axial measurement system;

Processing 06 of the above-mentioned signals to carry out:

A frequency analysis and a spectral processing 10 of the signals regarding the identification of the frequency content of the signals being detected and the frequency content detected at each axis of the multi-axial measurement system;

Identifying 08 motor activity, indices, physical quantities, biomarkers, other parameters regarding the motor state of the subject, together with the identification of temporal instants in which such motor state occur;

Comparing 12 predetermined parameters and indices with reference values, to verify whether the motor state matches a reference pattern to a predetermined degree.

Figure 2:
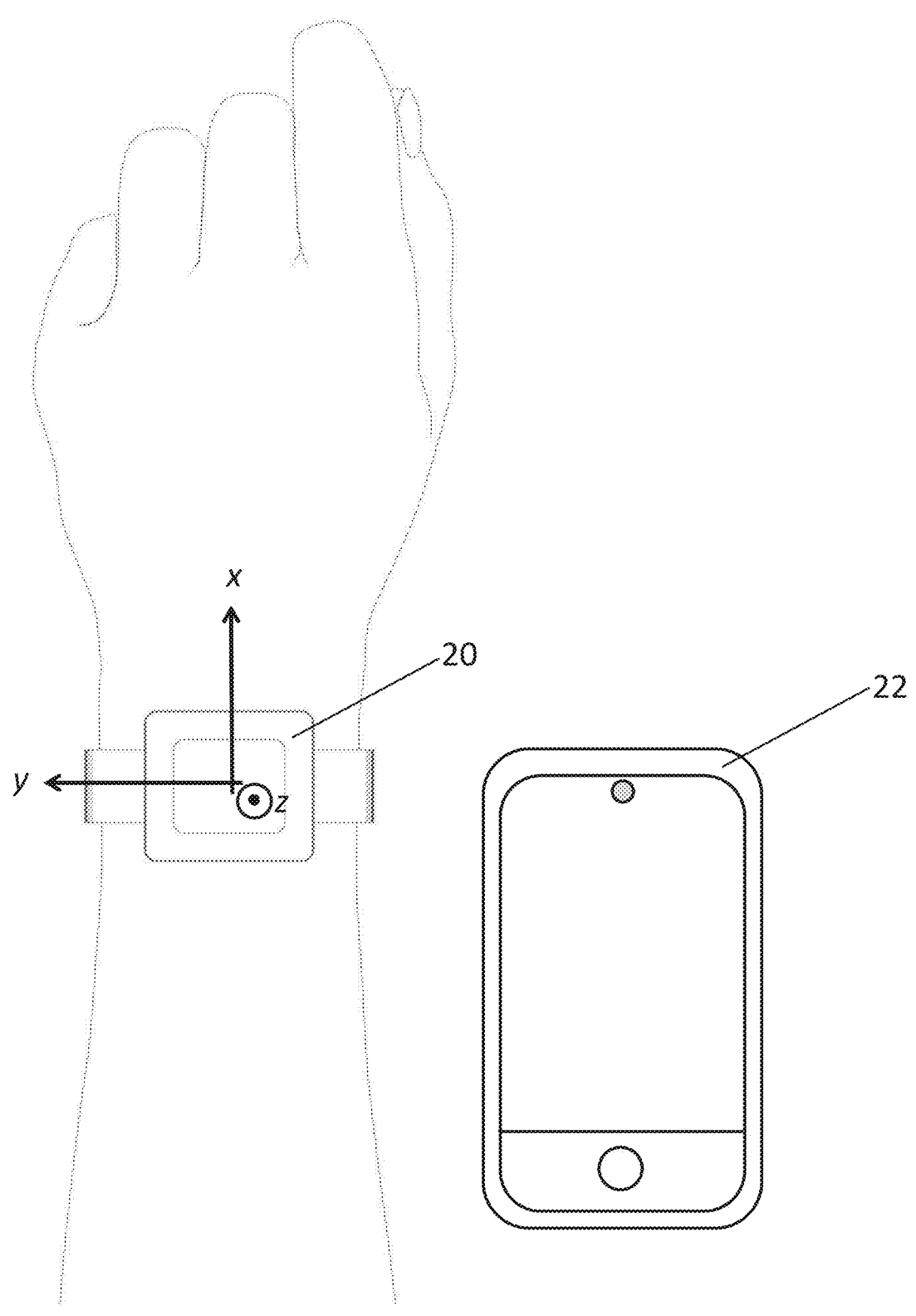
FIGS. 2, 2A and 2B schematically illustrate the main components of a wearable system according to the invention with respect to the detection and recording of information on the movement of body limbs and other parts of a patient's body.

FIG. 2 shows a preferred embodiment of the invention, where the wearable device for the determination of the motor state of a subject is a wrist-worn sensor configured as a wrist-watch; the device may include also a wireless connection with a smartphone.

In one embodiment, the detection 02 of signals containing information regarding the movement of body limbs and other parts of a patient's body takes place continuously over time and through a wearable multi-axial measurement system 20.

In one embodiment, measurements may take place continuously over time, for example, 24/24 h and 7/7, or durations lower than 24 hours, e.g. 12 or 16 hours, may be set to exclude hours of sleep or specific periods of the day. Such "passive" recording sessions are carried out during the execution of daily activity by the subject.

In another embodiment, measurements may take place during the execution of motor tests and exercises carried out by the subject (i.e. "active" recording sessions), for the total duration of such exercises, for example, tens of seconds, as reported below.

In another embodiment, in addition to, or as an alternative to the previous one, the signal processing 06 may include the use of a smoothing filter to process the sequence of synthetic numerical values, scores, and/or indices that have been detected. In a preferred embodiment, the smoothing filter is a mobile average filter.

As shown in FIG. 2, the wearable multi-axial measurement system may contain a tri-axial accelerometer worn on the patient's wrist like a watch. Alternatively, it may be wrapped around another body limb, for example, in the form of a belt or a strap.

FIG. 2 also shows the three sample axes (X, Y, Z) and in one embodiment, the data coming from each axis of the multi-axial measurement system are sampled at a representative rate of 50 Hz or 25 Hz for each axis.

In one embodiment, the multi-axial measurement system is a tri-axial accelerometer with a measuring range from −8 g to 8 g.

Figures 2A, 2B:
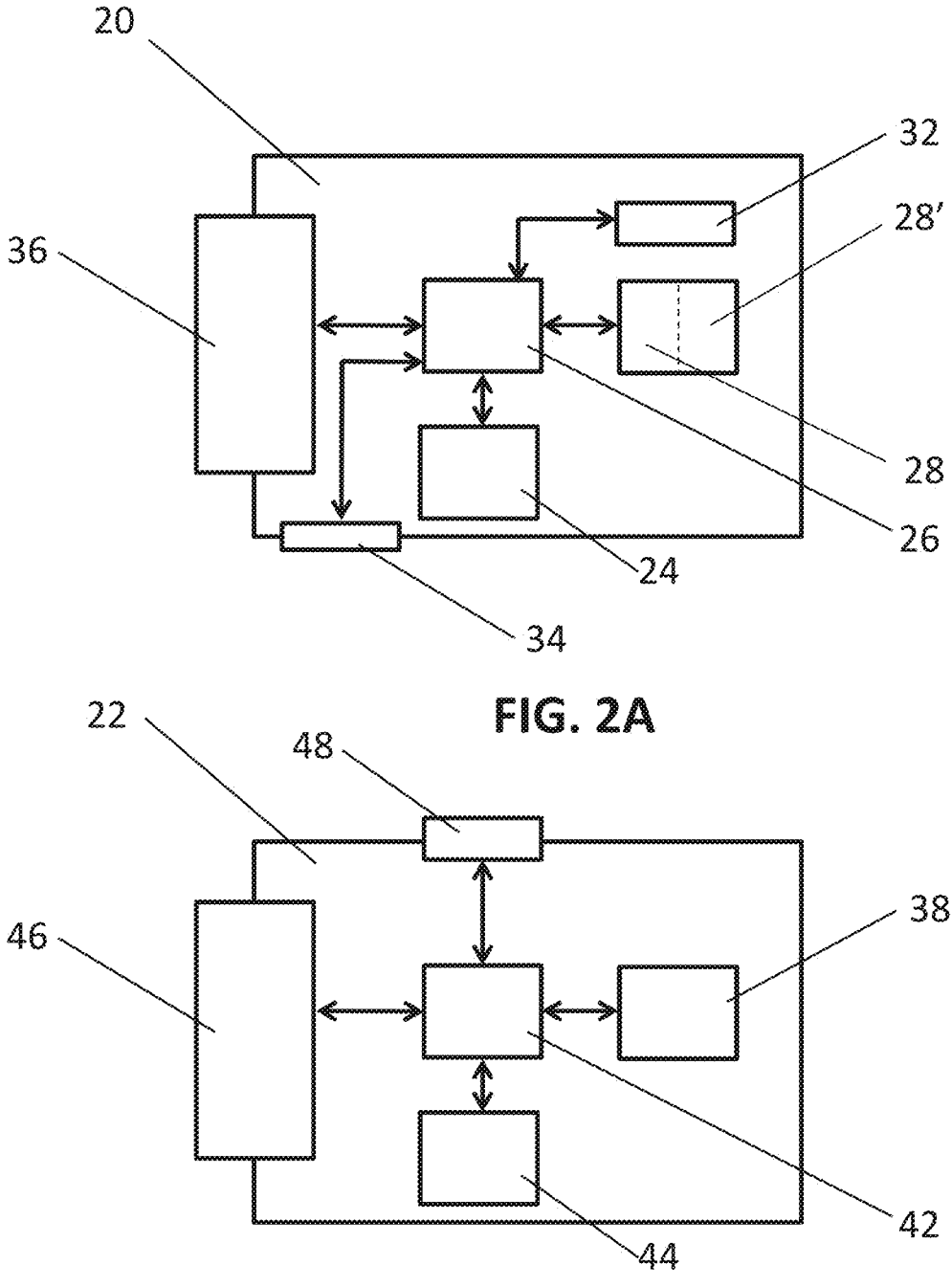

In a possible configuration of the invention, shown in FIG. 2A, the device 20 of FIG. 2 may therefore contain the following modules or internal devices:

A multi-axial measurement unit 28' for the detection over time of signals containing information on the movement of body limbs and other parts of a patient's body; a signal converter 28 may be included in the measurement unit 28' or may be an external unit and is configured to convert the signal into data.

A measurement unit 32 for the detection over time of a specific state of the apparatus (e.g. worn or not worn, working or not working, recording in progress) or other physiological parameters/processes, such as heart rate, near-body temperature, body positioning and walking;

A processing unit 26 for performing the pre-processing and processing of the signals;

A storage unit 24 that contains the data detected by the multi-axial measurement system and the results processed from the previous points;

Communication interfaces (based on wired and/or wireless units 34) to transfer the measured and processed information, together with the final results and the information on the ongoing acquisition and processing;

A user interface (based on a built-in display 36 or an external display) to interact with the user and to visualize the measured and processed information, together with the final results and the information on the ongoing acquisition and processing;

Output devices for communicating a reminder and/or the state of the apparatus and/or the power supply system to the patient;

Input devices for communicating a given event.

In one embodiment, the signal converter 28 and processing unit 26 for performing the pre-processing and processing of the data enable a rearrangement of data stored in the memory support 24 so that data are processed according to operations, which are disclosed later, and are subdivided into time sub-intervals, with the computation of various parameters for each sub-interval. In this embodiment, the intermediate data obtained after such processing operations are stored in the storage unit 24; finally, such signal converter 28 and processing unit 26 enable a rearrangement of intermediate data stored in the unit 24 in order to compute the final parameters and the final results, also as disclosed later.

The final results may be presented with textual and/or graphical elements.

In one embodiment, results of passive and/or active recordings may be presented that provide the final values of the computed parameters together with the indication of a reference range for each parameter; a textual element may be included to indicate the final results (e.g. motor conditions attributable/non-attributable to Parkinsonism).

Figure 5:
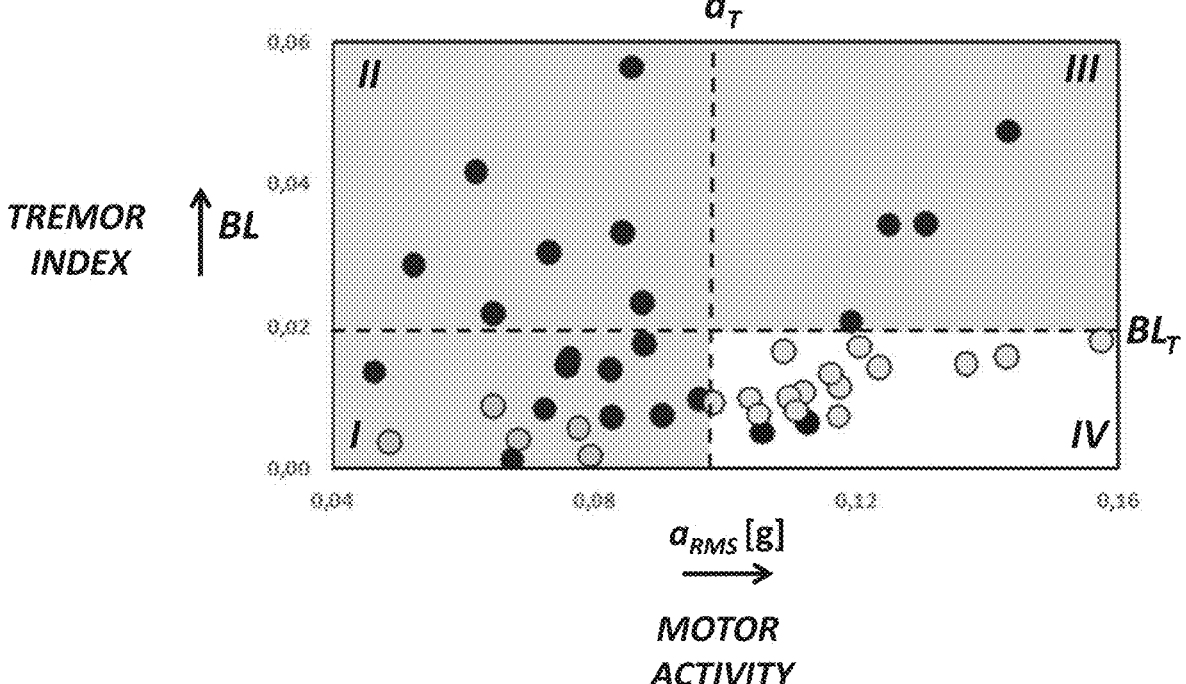
FIG. 5 schematically illustrates a possible representation of the results provided a device according to the invention arranged with a two-dimensional coordinate plane or Cartesian plane, where the two axes represent the values of $a_{RMS}$ and BL.

In another embodiment, the final results of the passive recording may be presented by providing a graphical element with the final values of the computed parameters according to the scheme reported in FIG. 5; such graphical element may be constituted of a two-dimensional coordinate plane or Cartesian plane, where the two axes represent the values of motor activity $a_{RMS}$ and tremor index BL, and the background color of such plane is shown in different colors in order to display the range of values related to healthy conditions (e.g. white background in FIG. 5) and to parkinsonism conditions (e.g. grey background in FIG. 5).

Similarly, the final results of the active recording may be presented providing a graphical element with the final values of the computed parameters according to the scheme reported in FIG. 5. In particular, results of the active tests on tremor and slowness/bradykinesia may be presented with a two-dimensional coordinate plane or Cartesian plane, where the two axes represent the values of motor activity $a_{RMS}$ and frequency f, and the background color of such plane is shown in different colors in order to display the range of values related to healthy conditions and non-healthy motor states conditions, e.g. related to tremor and slowness/bradykinesia; a textual element may be included to indicate the final results (e.g. motor conditions attributable/not attributable to Parkinsonism).

In another embodiment, the wearable device may be limited to perform the operations of detection 02 and pre-processing 04 (see FIG. 1), while the remaining and additional units that process this information and show results are external.

In this case, the wearable device includes a memory unit so that the multi-axial measurement data may be stored and then transferred, through a cable or wirelessly, to the external processing system (e.g. a computer, an external server or external smartphone 22, or a combination of such systems).

In one case, the external processing system may be an external smartphone and may include:

Communication interfaces (based on wired and/or wireless units 48) to communicate with the apparatus 20. The communication interfaces 48 may be configured to enable a wired communication system (for example, may use a USB protocol) and/or a wireless communication (for example, according to Bluetooth standards and/or an internet/long-term evolution (LTE) network);

An additional further measurement unit 38 for the detection over time of other physiological parameters or processes (e.g. step counter, walking);

A unit 42 for performing the pre-processing and processing of the signals and data;

A storage unit 44 that contains the data detected by the multi-axial measurement system and the results processed from the previous operations;

A graphic user interface (GUI) to interact with the apparatus 20 and a display 46 to visualize the final results and the information on the ongoing acquisition and processing;

A source code and/or software application to perform data processing according to the method described in the various above-described forms and to provide results and/or reports.

In another variant, the external processing system 22 may be based on the combination of an external smartphone and an external cloud computing architecture for storing, processing, and transmitting data. In this case, the data is transmitted using a transmission module of the communication interface 48, for example through an internet/LTE network, to a dedicated processing center. Data processed by the external processing center are then transmitted to the smartphone 22, where final results are provided to the subject with the display 46 and/or the display 36. In this case, a source code and/or software application to perform data processing according to the above-described method may be available on the processing center or both on the smartphone and on the processing center.

In another variant, the data is transmitted by means of the communication interface 34 of the apparatus 20, for example through an internet/LTE network, to a dedicated processing center. Data processed by the external processing center are then transmitted to the smartphone, where final results are provided to the subject by means of the display 46 and/or the display 36. In this case, a source code and/or software application to perform data processing according to the method described may be available on the processing center or both on the smartphone and on the processing center.

An aspect of the present invention relates to the processing mode of data obtained from multi-axial systems to accurately determine the motor state of a subject and to verify whether the motor state matches a reference pattern to a predetermined degree, where the reference pattern may be related to normal motor movements or to the typical motor signs of Parkinsonism, Parkinson's disease and movement disorders.

As reported below, in the preferred embodiment, such matching may be carried out by considering two indices, i.e. the average root mean square acceleration and the average ratio between two different values of the integrals of the power spectral density.

In one embodiment, within the processing 06, the recording sequence of each axis may be divided into time sub-intervals, of a duration $\Delta t$ between 1 second and 10 minutes, for each of which the parameters and Fourier transforms are computed. In the preferred embodiment, the recording sequence may be divided into time sub-intervals, of equal duration, from 4 seconds to 5 minutes, as the sub-intervals of the entire sequence, temporally synchronized for each axis of the triaxial accelerometer. Therefore, in this case, time sub-intervals of the same duration may be defined, each characterized by a start time and an end time; on each of these sub-intervals that make up the entire recording sequence, the Fourier transform is computed on each spatial axis as well as other parameters and indices.

In the preferred embodiment, the processing 06 include the processing of the at least one signal by subdividing a recording sequence, during which the at least one signal is collected, into time sub-intervals and computing the root mean square acceleration $a_{RMS,s}$ for each sample s:

$$a_{RMS,s}(t) = \sqrt{\frac{(a_{x,s}(t))^2 + (a_{y,s}(t))^2 + (a_{z,s}(t))^2}{3}}$$

and the average value of the root mean square acceleration $a_{RMS}(i)$ for each sub-interval i computed by considering the average of the time instant values $a_{RMS,s}$ for the entire time of the specific sub-interval:

$$a_{RMS}(i) = \frac{a_{RMS,1} + a_{RMS,2} + \dots + a_{RMS,N}}{N}$$

where:

N is the number of the samples in the time sub-interval;

i is an index used to identify each time sub-interval;

s is an index used to identify each the sample and, for each time sub-interval, has value from 1 to N;

$a_{x,s}(t)$ is the acceleration on the x-axis detected at time t corresponding to the sample s;

$a_{y,s}(t)$ is the acceleration on the y-axis detected at time t corresponding to the sample s;

$a_{z,s}(t)$ is the acceleration on the z-axis detected at time t corresponding to the sample s.

The average value of the root mean square acceleration may be considered as related to the motor activity of the subject. In another embodiment, processing 06 includes the detection of motor activity by calculating other parameters, such as activity counts or magnitude of the acceleration or other quantity related to the quantification of motor activity.

Figure 3:
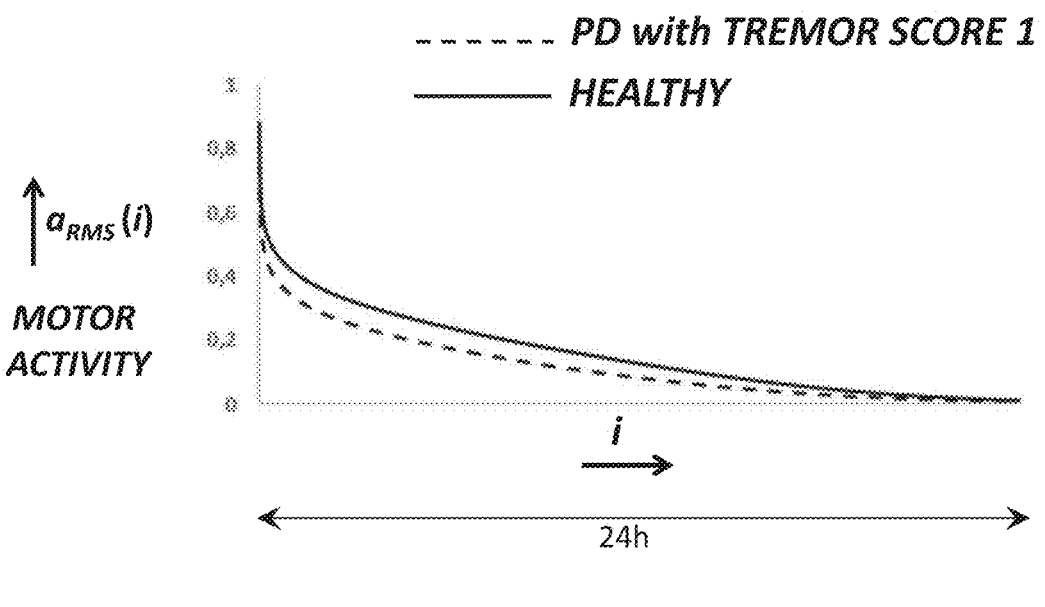
FIGS. 3 and 3A shows the typical values of $a_{RMS}(i)$ and $BL(i)$ determined for the time sub-intervals within a 24-hours recording period by considering a healthy subject and a PD patient; values of $a_{RMS}(i)$ and $BL(i)$ determined during the 24-recording are sorted from the highest to the lowest value.

FIG. 3 show the typical values of $a_{RMS}(i)$ determined for the time sub-intervals related to a 24-hours recording period by considering a healthy subject and a PD patient; values of $a_{RMS}(i)$ determined during the 24-recording are sorted from the highest to the lowest value.

Moreover, in such preferred embodiment, frequency analysis 10 includes the spectral processing of the at least one signal by subdividing a recording sequence, during which the at least one signal is collected, into time sub-intervals and computing a Fourier transform at each axis of the multi-axial measurement system, wherein the spectral processing determines a frequency content of a signal at each axis of the multi-axial measurement system.

In another embodiment, the spectral analysis of each sub-interval may include the use of the Fourier transform computation to perform a time-frequency analysis. This analysis may be performed by identifying the spectral density, power spectrum, power spectral density (Power Spectral Density, PSD), energy spectral density (Energy Spectral Density, ESD), acceleration spectral density (Acceleration Spectral Density, ASD), and other characteristic parameters deriving from the computation of the Fournier transform.

In the preferred embodiment, the spectral analysis of each sub-interval may include, for each axis, the computation of the power spectral density on each sub-interval and for each axis ($S_x$, $S_y$, $S_z$); in the same or in another embodiment, the time-frequency analysis performed on each sub-interval through the evaluation of power spectral density S calculated considering all the axes, e.g. the power spectral density of the multi-axial acceleration signal S or the sum of the values of the power spectral densities computed on each axis $S = S_x + S_y + S_z$, or the power spectral density of the mean quadratic value, calculated considering all the axes.

In one embodiment, spectral processing 10 may include the computation, evaluated for the individual time intervals and for each axis, of the spectral content by integrating the spectral densities S, $S_x$, $S_y$ and $S_z$ considering the various frequency ranges, including frequency ranges where motor signs of Parkinsonism, Parkinson's disease and neurodegenerative disorders typically occurs. In one embodiment, the spectral processing 10 may include the computation, evaluated for the individual time intervals, of the spectral content through the integration of the spectral densities S, $S_x$, $S_y$ and $S_z$:

Between 3 and 7 Hz, i.e. the interval in which Parkinsonian rest tremors typically occur, obtaining the $PSD_T$, $PSD_{Tx}$, $PSD_{Ty}$ and $PSD_{Tz}$ parameters respectively;

Overall frequency values or from 0 Hz to $f_s/2$, where $f_s$ is the sampling frequency, obtaining the $PSD_{TOT}$, $PSD_{TOTx}$, $PSD_{TOTy}$ and $PSD_{TOTz}$ parameters respectively.

In another embodiment, $PSD_T$ may be computed by the sum of the values $PSD_{Tx}$, $PSD_{Ty}$ and $PSD_{Tz}$, whereas $PSD_{TOT}$ may be computed by the sum of the values $PSD_{TOTx}$, $PSD_{TOTy}$ and $PSD_{TOTz}$.

In another embodiment, $PSD_T$ may be set equal to the maximum value between $PSD_{Tx}$, $PSD_{Ty}$ and $PSD_{Tz}$, whereas $PSD_{TOT}$ may be set equal to the maximum value between $PSD_{TOTx}$, $PSD_{TOTy}$ and $PSD_{TOTz}$ parameters.

In another embodiment, $PSD_T$ may be set equal to $PSD_{Tx}$ or equal to $PSD_{Ty}$, or equal to $PSD_{Tz}$, whereas $PSD_{TOT}$ may be set equal to $PSD_{TOTx}$, or equal to $PSD_{TOTy}$, or equal to $PSD_{TOTz}$.

In one embodiment, the processing 06 includes the identification, evaluated for each time sub-interval, of the movement pattern related to pronation-supination movement within a specific frequency range.

In the preferred embodiment, such frequency range is between 3 and 7 Hz; as a consequence of such identification procedure, the parameter BL(i) is determined for each time sub-interval:

if the presence of pronation-supination movement pattern within the specific frequency range is not determined in the time sub-interval i, the BL index for that time sub-interval is set to a zero value:

$$BL(i) = 0$$

if the presence of pronation-supination movement pattern within the specific frequency range is determined in the time sub-interval i, the BL index for that time sub-interval is equal to the ratio between the integral of power spectral density computed for the specific frequency range $PSD_T$ and the integral of power spectral density computed for the whole frequency range $PSD_{TOT}$ for that time sub-interval:

$$BL(i) = \frac{PSD_T(i)}{PSD_{TOT}(i)}$$

The parameter BL may be considered as related to the tremor at rest, and it has been shown that tremors at rest in Parkinson's disease are typically characterized by a pronation-supination movement between 3 and 7 Hz (J. JANCK-OVIC, Parkinson's disease: clinical features and diagnosis, Journal of Neurology, Neurosurgery and Psychiatry, 2008, doi:10.1136/jnnp.2007.131045). In another embodiment, processing 06 includes the detection of motor state associated with Parkinson's disease tremor by using other standard methods known in the art.

Similarly, the detection of the pronation-supination pattern may be carried out by using one or more standard methods known in the art; some examples of proposed methods for pronation-supination detection are reported in the following documents: IT 201700035240; U.S. Pat. No. 11,523,754 B2; FONG ET AL., Development of wrist monitoring device to measure wrist range of motion, IOP Conf. Series: Materials Science and Engineering 788, 2020, 012033 doi:10.1088/1757-899X/788/1/012033; OTTEN ET AL, A Framework to Automate Assessment of Upper-Limb Motor Function Impairment: A Feasibility Study. Sensors (Basel). 2015 Aug. 14; 15(8):20097-114. doi: 10.3390/s150820097; ABYARJOO ET AL., Monitoring Human Wrist Rotation in ThreeDegrees of Freedom, DOI:10.1109/SECON.2013.6567517.

In another embodiment, the pronation-supination pattern is detected if the following conditions occur:

$$\begin{cases} PSD_{Tx} > \tau_1 \\ PSD_{Ty} < \tau_2 \\ \tau_3 < PSD_{Tz} < \tau_4 \end{cases}$$

where $\tau_1$, $\tau_2$, $\tau_3$, $\tau_4$ are threshold values.

In another embodiment, the pronation-supination pattern is detected if the following condition occur:

$$\begin{cases} PSD_{Tx} > \tau_1 \\ PSD_{Ty} < \tau_2 \\ PSD_{Tz} > \tau_3 \end{cases}$$

Figure 3A:
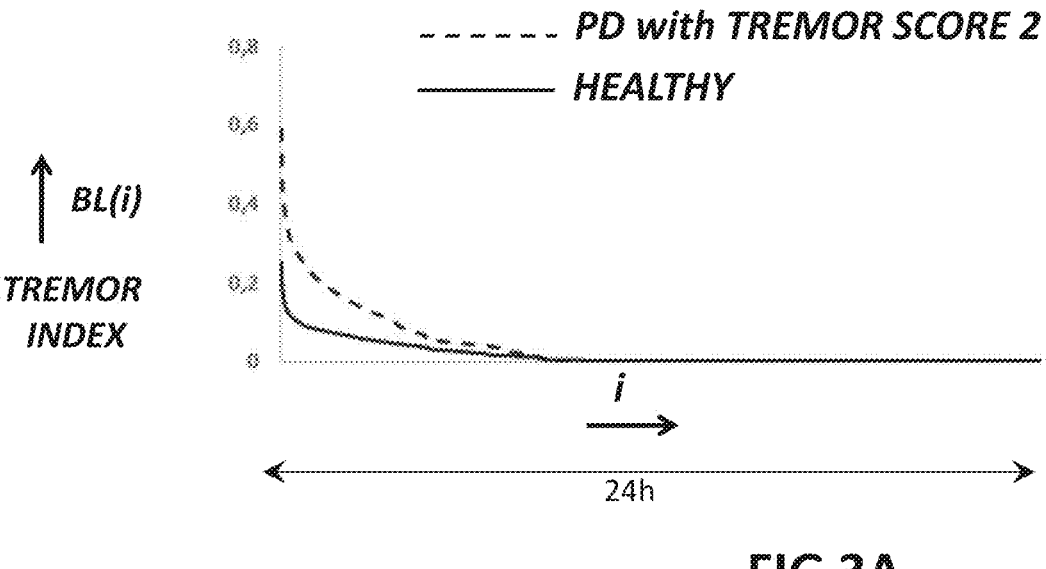

FIG. 3A show the typical values of BL(i) determined for the time sub-intervals related to a 24-hours recording period by considering a healthy subject and a PD patient; values of BL(i) determined during the 24-recording are sorted from the highest to the lowest value.

In the preferred embodiment, processing 06 includes the computation of $a_{RMS}$ and BL by calculating, respectively, the mean value of the $a_{RMS}(i)$ and BL(i) values detected for all sub-time intervals M:

$$a_{RMS} = \frac{1}{M} \sum_{i=1}^{M} a_{RMS}(i)$$

$$BL = \frac{1}{M} \sum_{i=1}^{M} BL(i)$$

where:
M is the number of time sub-intervals of the recording sequence;
i is an index used to identify each time sub-interval and has value from 1 to M.

In one embodiment, comparison 12 includes an evaluation both of the value $a_{RMS}$ against a reference value or interval and of the value BL against a reference value or interval, to verify whether the determined motor state matches the reference pattern to a predetermined degree.

In the preferred embodiment, two comparisons are carried out:

the determined value $a_{RMS}$ is compared against a reference value, i.e. the threshold $a_T$;

the determined value BL is compared against a reference value, i.e. the threshold $BL_T$, and if the following both conditions occur:

$$\begin{cases} a_{RMS} < a_T \\ BL > BL_T \end{cases}$$

The motor state is related to the presence of the motor signs related to Parkinsonism; vice versa, if the both of the above-reported conditions do not occur, the motor state is related to the absence of motor conditions that may be attributed to Parkinsonism.

The preceding condition on the BL parameter is mainly related to the tremor at rest, whereas the preceding condition on the $a_{RMS}$ parameter might include various motor aspects and various aspects of Parkinsonism and PD, including slowness/bradykinesia and rigidity.

In another embodiment, the determined values of $a_{RMS}$ and BL are respectively compared to one or more reference ranges.

It should be noted that the present invention is related to the determination of the motor state by taking into account the combination of two different comparisons, the first one related to motor activity or $a_{RMS}$ and the second one related to tremor index or BL.

In fact, the performances achievable by using only one comparison are worse than using both parameters.

As an example, FIGS. 3, 3A, 4 and 4A show the results of an illustrative test according to the present invention by considering a data set of 44 subjects, of which 24 patients had early PD and 20 healthy subjects.

Figures 4, 4A:
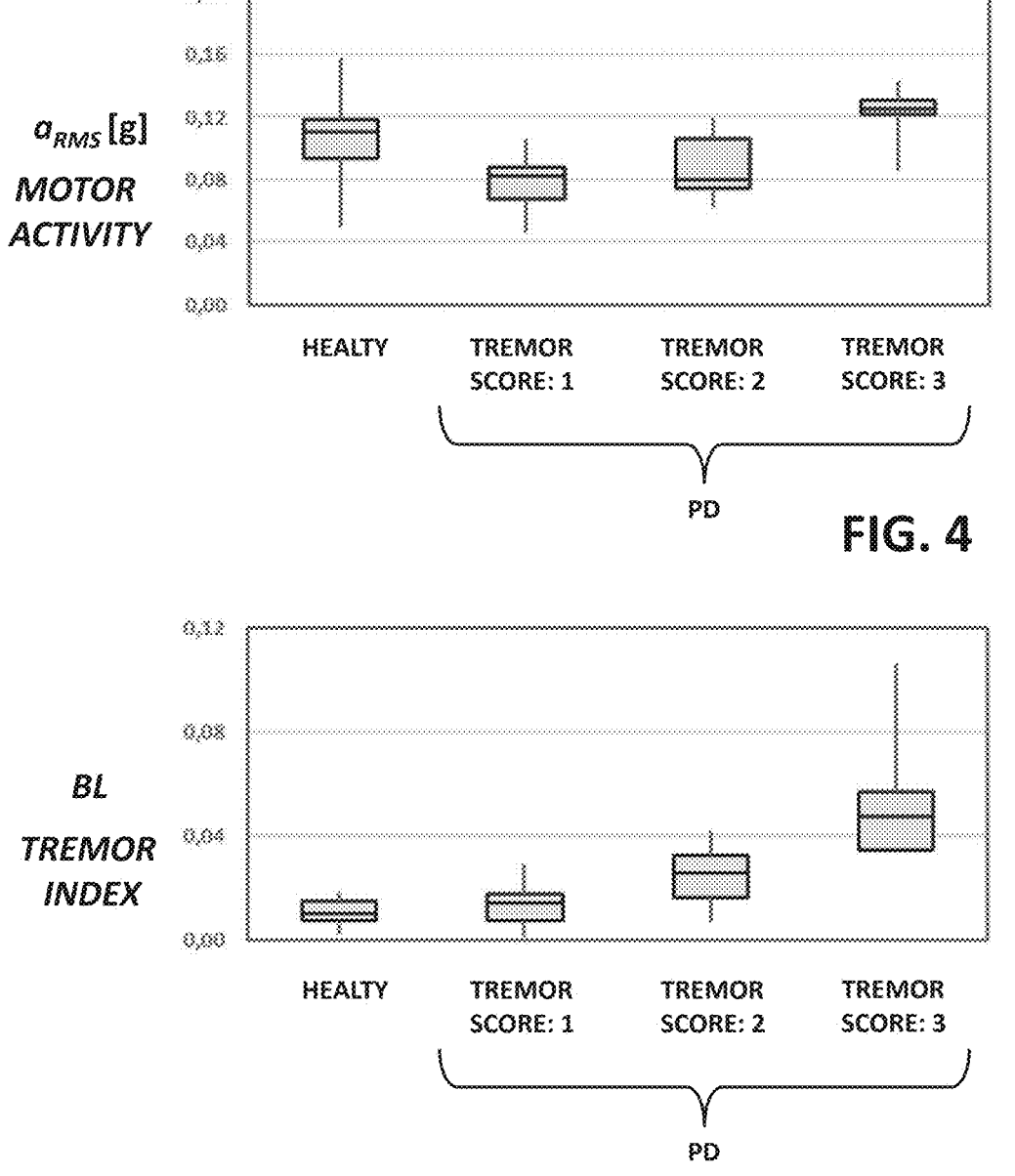
FIGS. 4 and 4A show the box plots of typical values of $a_{RMS}$ and BL in healthy subjects and in PD patients with a different severity of rest tremor; the severity of tremor in these figures is reported by considering the information obtained during MDS-UPDRS scoring for the item 3.17 "Rest tremor amplitude". Description of scores: 0=normal, 1=slight, 2=mild, 3=moderate, 4=severe.

FIG. 4 shows the box plots of the typical values of $a_{RMS}$ in healthy subjects and in PD patients with a different severity of rest tremor; all the continuous recording sessions of the subjects have a duration equal to 24 hours. The severity of tremor in the Figures is reported by considering the information obtained during MDS-UPDRS scoring for the item 3.17 "Rest tremor amplitude". In such scoring scale, the following ratings are considered:

A score equal to zero corresponds to "Normal" (i.e. "no tremor");

A score equal to 1 corresponds to "Slight" tremor;

A score equal to 2 corresponds to "Mild" tremor;

A score equal to 3 corresponds to "Moderate" tremor;

A score equal to 4 corresponds to "Severe" tremor.

As shown in FIG. 4, the typical values of $a_{RMS}$ in healthy subjects may overlap the typical values of $a_{RMS}$ in PD subjects with mild-to-moderate tremor, so that evaluating only the motor activity of data measured by sensors could be not sufficient to reasonably and accurately distinguish healthy people from PD patients with mild to moderate tremor.

In order to determine how well the motor activity may separate PD and control subject, the AUC-ROC metric (Area Under The Curve-Receiver Operating Characteristics) was used and the following results were obtained:

the value of AUC is equal to 0.626;

various threshold settings were considered; for the $a_{RMS}$ threshold value that maximizes the value for the accuracy, the following performances were obtained:

$$ACCURACY = (TP + TN)/(TP + TN + FP + FN) = 0.73$$

$$SENSITIVITY = TP/(TP + FN) = 0.71$$

-continued $$SPECIFICITY = TN/(TN + FP) = 0.75$$

$$F1 - SCORE = 2TP/(2TP + FP + FN) = 0.67$$

$$K = 2*(TP*TN - FN*FP)/[(TP + FP)*(FP + TN) +$$

$$(TP + FN)*(FN + TN)] = 0.45$$

where:

TP is the number of true positive results, i.e. TP is a test result that correctly indicates the presence of Parkinsonism;

TN is the number of true negative results, i.e. TN is a test result that correctly indicates the absence of Parkinsonism;

FP is the number of false positive results, i.e. FP is a test result which wrongly indicates that Parkinsonism is present;

FN is the number of false negative results, i.e. TP is a test result which wrongly indicates that Parkinsonism is absent;

K is Cohen's kappa coefficient.

Finally, according to the statistical analysis of data reported in FIG. 4, the magnitude of the motor activity $a_{RMS}$ was higher in healthy patients than in PD patients with slight tremor at rest (score 1 at item 3.17 of MDS-UPDRS), whereas motor activity $a_{RMS}$ did not significantly differ between controls and PD patients with mild-to-moderate tremor rest (score 2 to 3 at item 3.17 of MDS-UPDRS).

Similarly, FIG. 4A shows the typical values of BL in healthy subjects and in PD patients with a different severity of rest tremor. In this case, the typical values of BL in healthy subjects may overlap with the typical values of BL in PD subjects with slight tremor, so that evaluating only the contribution of BL or rest tremor of data measured by sensors could be not enough to reasonably and accurately distinguish healthy people from PD patients with mild to moderate tremor.

In order to determine how well the BL index may separate PD and control subject, the AUC-ROC metric was used and the following results were obtained:

the value of AUC is equal to 0.701;

various threshold settings were considered; for the BL threshold value that maximizes the value for the accuracy, the following performances were obtained:

$$ACCURACY = 0.73$$

$$SENSITIVITY = 0.50$$

$$SPECIFICITY = 1.00$$

$$F1-SCORE = 0.67$$

$$K = 0.48$$

According to the statistical analysis of data reported in FIG. 4A, the magnitude of the tremor index BL was smaller in controls than in PD patients with mild-to-moderate tremor rest and did not significantly differ between controls and PD patients with slight tremor at rest.

A similar analysis was carried out by considering not only one parameter, but taking into account both the comparison of the $a_{RMS}$ values and the comparison of the BL values. By using both parameters is possible to significantly improve distinguishing healthy people from PD patients, and the following performances were obtained for the combination of $a_{RMS}$ and BL threshold values (i.e. $a_T$ and $BL_T$) that maximize the value for the accuracy:

$$\text{ACCURACY} = 0.84$$

$$\text{SENSITIVITY} = 0.92$$

$$\text{SPECIFICITY} = 0.75$$

$$F1\text{-SCORE} = 0.86$$

$$K = 0.68$$

From above-reported data it clearly emerges that the combination of the two different digital biomarkers allows obtaining a result which is much better than the use of just one parameter, indeed it allows taking into account the simultaneous presence and effect of the main cardinal motor manifestations of Parkinsonism.

In particular, the preceding analysis show that the performances and accuracy obtained by using both parameters, i.e. the motor activity $a_{RMS}$ and the tremor index BL, are better than the performances and accuracy values obtainable by using just one of the two above quoted digital biomarkers, confirming the improvement achievable by the present invention based on the combination of different comparisons (e.g. accuracy is up to 73% if just one index is considered and raises to 84% by considering both parameters, whereas Cohen's kappa coefficient raises from 48% to 68%, corresponding to a substantial agreement instead of a moderate agreement).

Therefore, such combination of parameters/digital biomarkers can allow taking advantage of the complementary aspects of both parameters (e.g. of the high capability of motor activity $a_{RMS}$ in distinguishing controls from PD patients with slight tremor and the high capabilities of the tremor index BL in distinguishing controls from PD patients with mild-to-moderate tremor).

It should be noted that the motor activity of a subject is a global parameter having a final magnitude that may be influenced by various factors, e.g. a voluntary movement of a limb during normal daily life, steps and walking, and pathological movements/aspects such as tremor, dyskinesia and rigidity.

Therefore, the tremor index BL could be used to separate the contribution of tremor from the global value of the motor activity, refining the opportunity to distinguish healthy people from PD patients with tremor and the occurrence of False Negative recordings.

In one embodiment, the results obtained with the present invention may be provided with a two-dimensional coordinate plane or Cartesian plane, where the two axes represent the values of $a_{RMS}$ and BL.

FIG. 5 show the test results for the above mentioned 44 subject; the areas labeled as I, II and III (grey background) are referred to values for $a_{RMS}$ and BL corresponding to test results where the determined motor state is associated with the presence of the motor signs related to Parkinsonism, whereas the area IV (white background) refers to test results where the determined motor state is related to the absence of motor conditions attributable to Parkinsonism.

In FIG. 5 the black dots over grey background are true positives, the black dots over white background are false negatives, the dark grey dots over grey background are false positives, the dark grey dots over white background are true negatives.

In one embodiment, in addition to the passive recording session previously reported, e.g. continuous acquisition for 16 hours per day or 24 hours per day performed during daily motor activity of the subject, one or more further recording sessions are performed; these recording sessions may be considered as a complementary step to the operations described up to now.

In one embodiment, as already discussed above, in addition to the passive recording section described up to now and schematically reported in FIG. 1, FIG. 3 and FIG. 5, one or more "active" recording sessions are carried out during the execution of specific motor tests described in the MDS-UPDRS rating scale or similar to the ones described in such rating scale in order to assess motor manifestations related to neurodegenerative diseases. Therefore, such "active" recording sessions are carried out during the execution of specific and predetermined motor tests carried out by the subject for a time-limited duration.

Each active recording session is carried out according to the same scheme reported in FIG. 1, including the operations related to detection 02, pre-processing 04, processing 06 and comparison 12, as described below.

Figure 6:
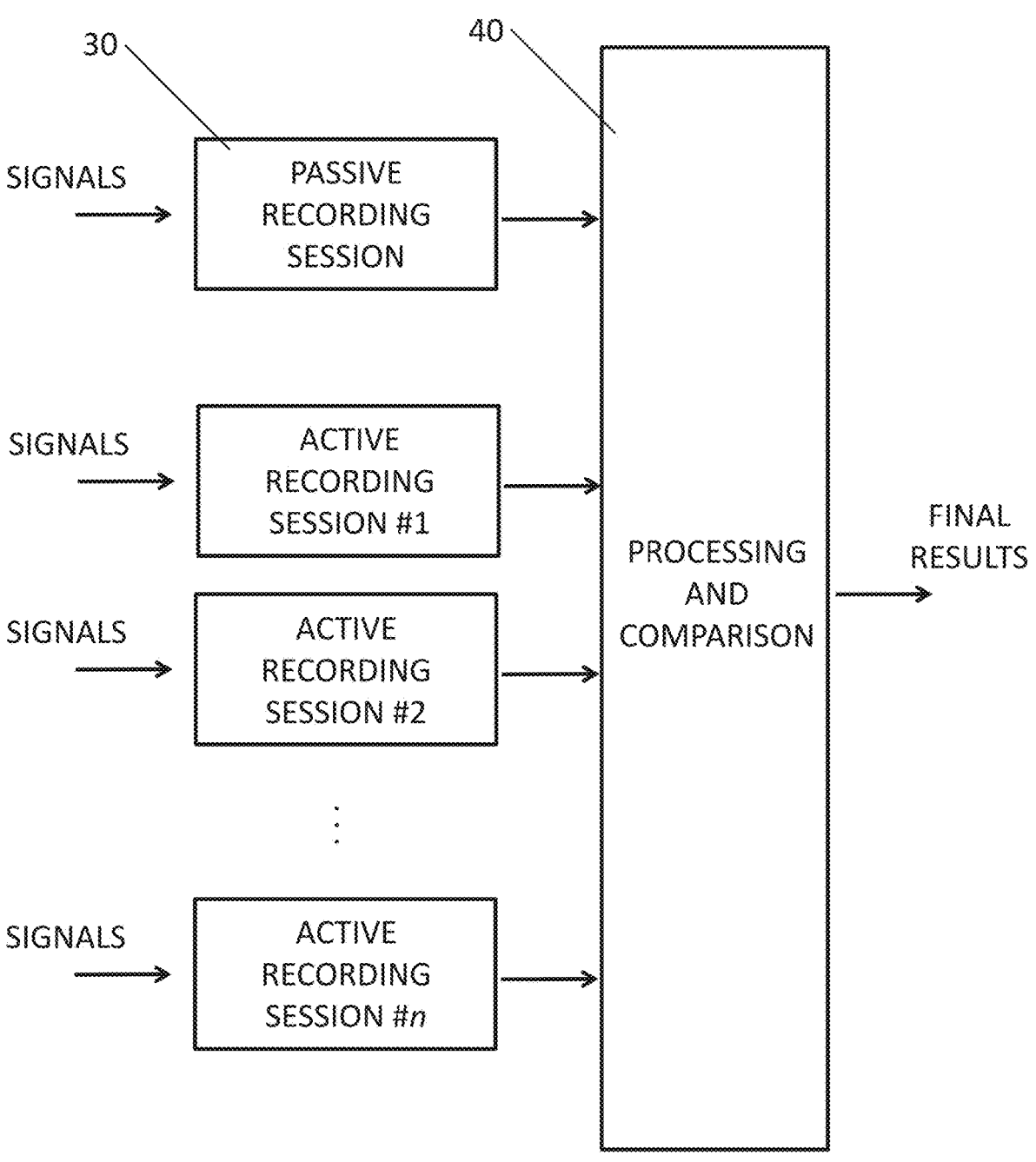
FIG. 6 schematically illustrates an exemplary situation in which one passive recording session and more active recording session (e.g. from the session #1, to the session #n) are carried out.

FIG. 6 shows an exemplary embodiment in which one passive recording session 30 and more active recording sessions are carried out. The passive recording session 30 is based on the operations previously described and also reported in FIG. 1.

In one embodiment, one or more passive recording session(s) and/or one or more active recording session(s) are carried out; in the preferred embodiment, one passive recording session is carried out, for one or more days or weeks, and if the result is a motor state related to the absence of motor conditions attributable to Parkinsonism, one or more active recording session(s) are executed by the subject. Such condition or other conditions may be determined by specific operations 40 related to processing and comparisons of the results of the various recording sessions. Such recording session may be related to one or more limbs or to a plurality of parts of a body of the subject.

In another embodiment, active recording sessions may be performed before, during or after the passive recording session(s); the possible execution of the active sessions may be dependent or independent on the result of the other sessions and may also be implemented by specific operations 40 related to processing and comparisons of the results of the various recording sessions.

In this case of "active" acquisition, each recording session has a duration in the order of tens of seconds, e.g. 10 or 30 or 60 seconds, or lower. In one embodiment, the measurements are carried out during the execution of the motor tests related to the assessment of slowness/bradykinesia (e.g., finger tapping (MDS-UPDRS 3.4), hand movements (3.5), pronation-supination movements (3.6), toe tapping (3.7), and foot tapping (3.8)), rigidity, tremor at rest (e.g. amplitude (3.17) and constancy (3.18)), kinetic and postural tremor (3.15, 3.16), gait and freezing of gait (3.10, 3.11)).

In the preferred embodiment, detection 02 and the operations reported in FIG. 1 are carried during one to four recording sessions related to the following motor tests:

hand movements (3.5), pronation-supination movements (3.6), rest tremor amplitude (3.17), postural tremor (3.15).

In this preferred embodiment, pre-processing 04 of such signals is performed to limit the frequency band and to exclude any possible peak at 0 Hz or DC component. In such embodiment, processing 06 may be carried out by considering one or more time sub-intervals for each recording session (i.e. M=1 or M>1); alternatively, each time sub-interval may include one or more samples of the detected signals 02.

In the preferred embodiment, processing 06 includes the processing of the at least one signal and computing the root mean square acceleration $a_{RMS,s}$ for each sample s, the average value of the root mean square acceleration $a_{RMS}(i)$ for each sub-interval i and/or the computation of the average value of the root mean square acceleration $a_{RMS}$ by calculating the mean value of the $a_{RMS}(i)$ or $a_{RMS,s}$ respectively (e.g. as reported above, in one embodiment related to active recording sessions, M is set equal to 1, therefore $a_{RMS}$ and $a_{RMS}$ (i=1) correspond to the mean value of the $a_{RMS,s}$ values by considering all samples of the detected signal).

Figure 7:
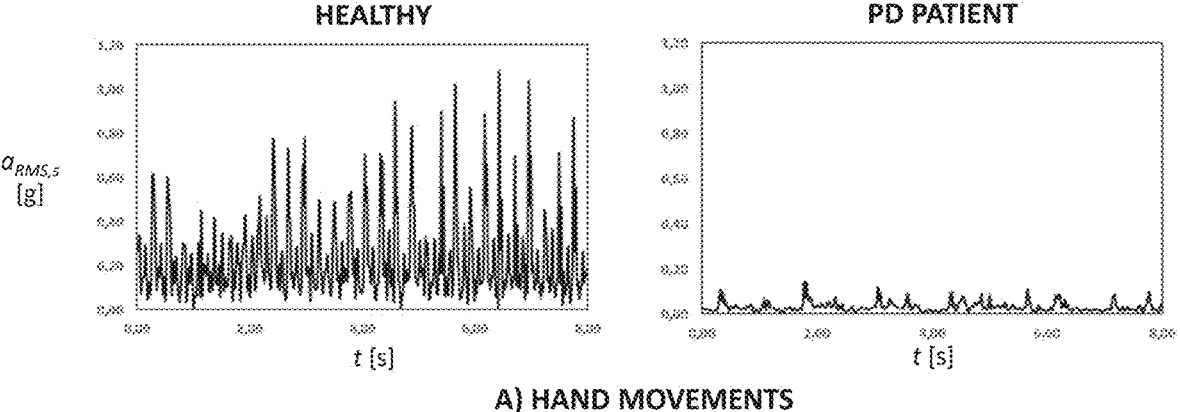
FIG. 7 shows an example of the temporal patterns of $a_{RMS,s}$ determined during the execution of the motor tests on hand movements (A) and pronation-supination (B) in a normal subject (left column) and in a subject with PD (right column).
Figure 7:
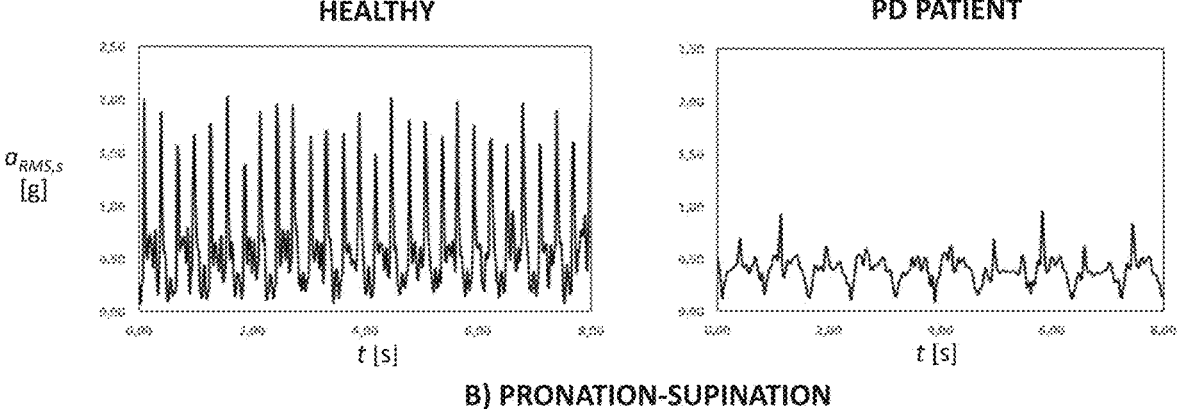

FIG. 7 and FIG. 8 show an example of the temporal patterns of $a_{RMS,s}$ determined during the execution of the four above quoted motor tests in a normal subject and in a subject with PD.

Moreover, in such preferred embodiment, the frequency analysis 10 include the spectral processing of the at least one signal and computing a Fourier transform at each axis of the multi-axial measurement system, wherein the spectral processing determines a frequency content of a signal at each axis of the multi-axial measurement system. In such embodiment, the frequency analysis 10 includes computing, for each axis and/or for the entire vector signal, the Fourier transform of the time-acceleration signals at each axis of the accelerometer $A_x$, $A_y$, $A_z$, the frequency peaks occurring in a specific frequency range and calculating the amplitude $A_P$ and the frequency value $f_P$ of each frequency peak of the vector signal and/or calculating, for each axis, the amplitude $A_{P,x}$, $A_{P,y}$, $A_{P,z}$ and the frequency value $f_{P,x}$, $f_{P,y}$, $f_{P,z}$ of each frequency peak. In another embodiment, the following parameters are also computed:

$A_{AVG}$, the average value of the values of the Fourier transforms $A_x$, $A_y$, $A_z$, in the range between 3 Hz and 7 Hz;

$A_{MAX}$, the maximum value of the Fourier transforms $A_x$, $A_y$, $A_z$, in the range between 3 Hz and 7 Hz.

In the preferred embodiment and with reference to the recording sessions carried out during the motor tests on pronation-supination movements (3.6), comparison 12 include an evaluation both on the value $a_{RMS}$ against a reference value or interval and on the value $f_{P,z}$ against a reference value or interval, to verify whether the determined motor state matches the reference pattern to a predetermined degree. In this embodiment, two comparisons are carried out:

the determined value $a_{RMS}$ is compared against a reference value, i.e. the threshold $a_{T,B}$;

the determined value $f_{P,z}$ is compared against a reference value, i.e. the threshold $f_{P,B}$, and if both of the following conditions occur:

$$\begin{cases} a_{RMS} < a_{T,B} \\ f_{P,z} < f_{P,B} \end{cases}$$

the motor state is related to the presence of motor conditions attributable to slowness/bradykinesia; vice versa, the motor state is related to the absence of motor conditions attributable to slowness/bradykinesia.

In another embodiment, comparison 12 may include an evaluation of the $A_{P,z}$ value instead of on $a_{RMS}$.

In another embodiment, comparison 12 includes an evaluation of the value $a_{RMS}$ against a reference value (e.g. the threshold $a_{T,B}$) or interval, to verify whether the determined motor state matches the reference pattern to a predetermined degree.

In another embodiment, the comparison 12 include an evaluation on one or more of the determined parameters (e.g. $a_{RMS}$, $f_P$, $A_P$, $A_{P,x}$, $A_{P,y}$, $A_{P,z}$, $f_{P,x}$, $f_{P,y}$, $f_{P,z}$) against one or more reference values or intervals, to verify whether the motor state determined matches the reference pattern to a predetermined degree.

FIG. 9A shows an example of the Fast Fourier Transform $A_z$ of $a_{z,s}(t)$ determined during the execution of the motor tests on pronation-supination movements in a normal subject and in a subject with PD.

Similarly, in the preferred embodiment and with reference to the recording sessions carried out during the motor tests on hand movements (3.5), the comparison 12 includes an evaluation both of the value $a_{RMS}$ against a reference value or interval and on the value $f_{P,y}$ against a reference value or interval, to verify whether the determined motor state matches the reference pattern to a predetermined degree. In this embodiment, two comparisons are carried out: the determined value $a_{RMS}$ is compared against a reference value, i.e. the threshold $a_{T,C}$:

the determined value $f_{P,Y}$ is compared against a reference value, i.e. the threshold $f_{P,C}$.

and if the following both conditions occur:

$$\begin{cases} a_{RMS} < a_{T,C} \\ f_{P,y} < f_{P,C} \end{cases}$$

the motor state is related to the presence of motor conditions attributable to slowness/bradykinesia; vice versa, the motor state is related to the absence of motor conditions attributable to slowness/bradykinesia.

In another embodiment, comparison 12 may include an evaluation of the $A_{P,y}$ value instead of $a_{RMS}$.

In another embodiment, comparison 12 includes an evaluation on the value $a_{RMS}$ against a reference value (e.g. the threshold $a_{T,C}$) or interval, to verify whether the motor state determined matches the reference pattern to a predetermined degree.

In another embodiment, comparison 12 includes an evaluation of one or more of the determined parameters (e.g. $a_{RMS}$, $f_P$, $A_P$, $A_{P,x}$, $A_{P,y}$, $A_{P,z}$, $f_{P,x}$, $f_{P,y}$, $f_{P,z}$) against one or more reference values or intervals, to verify whether the determined motor state matches the reference pattern to a predetermined degree.

In the preferred embodiment and with reference to the recording sessions carried out during the motor tests on tremor amplitude (3.17), comparison 12 includes an evaluation both of the value $a_{RMS}$ against a reference value or interval and of the value $f_{P,y}$ against a reference value or interval, to verify whether the determined motor state matches the reference pattern to a predetermined degree. In this embodiment, two comparisons are carried out:

the determined value $a_{RMS}$ is compared against a reference value, i.e. the threshold $a_{T,T}$;

the determined value $f_{P,y}$ is compared against a reference interval, i.e. the interval between the thresholds $f_{P,TL}$ and $f_{P,TH}$.

and if both of the following conditions occur:

$$\begin{cases} a_{RMS} > a_{T,T} \\ f_{P,TL} \le f_{P,y} \le f_{P,TH} \end{cases}$$

the motor state is related to the presence of motor conditions attributable to tremor at rest; vice versa, the motor state is related to the absence of motor conditions attributable to tremor at rest.

In the preferred embodiment, the characteristic frequency content, defined by $f_{P,TL}$ and $f_{P,TH}$, may include, for example, the frequencies included in the intervals between 3 and 7 Hz.

In another embodiment, comparison 12 may include an evaluation on the $A_{P,y}$ value instead of on $a_{RMS}$.

In another embodiment, the comparison 12 includes an evaluation on the value $A_{AVG}$ against a reference value (e.g. the threshold value $A_{AVG,T}$) or interval, to verify whether the motor state that has been determined matches the reference pattern to a predetermined degree.

In another embodiment, the comparison 12 includes an evaluation on the value $A_{MAX}$ against a reference value (e.g. the threshold value $A_{MAX,T}$) or interval, to verify whether the motor state that has been determined matches the reference pattern to a predetermined degree.

In another embodiment, comparison 12 includes an evaluation of one or more of the determined parameters (e.g. $a_{RMS}$, $f_P$, $A_P$, $A_{P,x}$, $A_{P,y}$, $A_{P,z}$, $f_{P,x}$, $f_{P,y}$, $f_{P,z}$, BL, PSD, $PSD_T$, $PSD_{Tx}$, $PSD_{Ty}$, $PSD_{Tz}$, $PSD_{TOT}$, $PSD_{TOTx}$, $PSD_{TOTy}$, $PSD_{TOTz}$) against one or more reference values or intervals, to verify whether the determined motor state matches the reference pattern to a predetermined degree.

FIG. 9B shows an example of the Fast Fourier Transform $A_y$ of $a_{y,s}(t)$ determined during the execution of the motor tests on tremor at rest in a normal subject and in a subject with PD.

Similarly, in the preferred embodiment and with reference to the recording sessions carried out during the motor tests on postural tremor (3.15), the comparison 12 include an evaluation both of the value $a_{RMS}$ against a reference value or interval and of the value $f_{P,z}$ against a reference value or interval, to verify whether the determined motor state matches the reference pattern to a predetermined degree. In this embodiment, two comparisons are carried out:

the determined value $a_{RMS}$ is compared against a reference value, i.e. the threshold $a_{T,P}$;

the determined value $f_{P,z}$ is compared against a reference interval, i.e. the interval between the thresholds $f_{P,PL}$ and $f_{P,PH}$.

and if both of following conditions occur:

$$\begin{cases} a_{RMS} > a_{T,P} \\ f_{P,PL} \le f_{P,z} \le f_{P,PH} \end{cases}$$

the motor state is related to the presence of motor conditions attributable to tremor at rest; vice versa, the motor state is related to the absence of motor conditions attributable to tremor at rest.

In one embodiment, the characteristic frequency content, defined by $f_{P,PL}$ and $f_{P,PH}$, may include, for example, the frequencies included in the intervals between 3 and 7 Hz.

In another embodiment, the comparison 12 may include an evaluation on the $A_{P,z}$ value instead of on $a_{RMS}$.

In another embodiment, the comparison 12 includes an evaluation of the value $a_{RMS}$ against a reference value (e.g. the threshold $a_{T,P}$) or interval, to verify whether the determined motor state matches the reference pattern to a predetermined degree.

In still another embodiment, the comparison 12 includes an evaluation on the value $A_{AVG}$ against a reference value (e.g. the threshold value $A_{AVG,T}$) or interval, to verify whether the motor state that has been determined matches the reference pattern to a predetermined degree.

In yet another embodiment, the comparison 12 includes an evaluation on the value $A_{MAX}$ against a reference value (e.g. the threshold value $A_{MAX,T}$) or interval, to verify whether the motor state that has been determined matches the reference pattern to a predetermined degree.

In another embodiment, comparison 12 include an evaluation on one or more of the determined parameters (e.g. $a_{RMS}$, $f_P$, $A_P$, $A_{P,x}$, $A_{P,y}$, $A_{P,z}$, $f_{P,x}$, $f_{P,y}$, $f_{P,z}$, BL, PSD, $PSD_T$, $PSD_{Tx}$, $PSD_{Ty}$, $PSD_{Tz}$, $PSD_{TOT}$, $PSD_{TOTx}$, $PSD_{TOTy}$, $PSD_{TOTz}$) against one or more reference values or intervals, to verify whether the determined motor state matches the reference pattern to a predetermined degree.

In the most preferred embodiment, detection 02 and the operations reported in FIG. 1 are carried during two recording sessions related to the following motor tests:

pronation-supination movements (3.6), rest tremor amplitude (3.17), and, if all of the four following conditions occur:

during pronation-supination movements recording session:

$$\begin{cases} a_{RMS} < a_{T,B} \\ f_{P,z} < f_{P,B} \end{cases}$$

and, during rest tremor amplitude recording session:

$$\begin{cases} a_{RMS} > a_{T,T} \\ f_{P,TL} \le f_{P,y} \le f_{P,TH} \end{cases}$$

the motor state is related to the presence of the motor signs related to tremor at rest and slowness/bradykinesia. Vice versa, if both of the above-reported conditions do not occur, the motor state is related to the absence of motor conditions attributable to slowness/bradykinesia and tremor at rest.

In another embodiment, the detection 02 and the operations reported in FIG. 1 are carried during two recording sessions related to the following motor tests:

pronation-supination movements (3.6), rest tremor amplitude (3.17), and, if all of the three following conditions occur:

during pronation-supination movements recording session:

$$\begin{cases} a_{RMS} < a_{T,B} \\ f_{P,z} < f_{P,B} \end{cases}$$

and, during rest tremor amplitude recording session:

$$A_{AVG} > A_{AVG,T}$$

21 the motor state is related to the presence of the motor signs related to tremor at rest and slowness/bradykinesia. Vice versa, if both of the above-reported conditions do not occur, the motor state is related to the absence of motor conditions attributable to slowness/bradykinesia and tremor at rest.

In another embodiment, the detection 02 and the operations reported in FIG. 1 and described above are carried during one or more recording sessions related to motor tests as described in the MDS-UPDRS or other similar motor tests for the assessment of the cardinal motor manifestations of Parkinsonism, Parkinson's disease and other neurodegenerative disease.

Furthermore, in another embodiment, the results of such operations carried out during the execution of the above quoted motor tests according to MSD-UPDRS or similar assessment may be used to confirm results of the continuous recording session.

The present invention, although preferably directed towards the determination of motor signs due to neurodegenerative diseases, may also be used to determine any motor state of a subject, even for non-diagnostic/therapeutic or medical purposes.

While the invention has been described in connection with the above-described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become obvious to those skilled in the art and the scope of the present invention is limited only by the appended claims.

The invention claimed is:

1. A system configured to determine a motor state of a subject, the system comprising:
   a wearable device;
   a sensor arranged in the wearable device, the sensor comprising a multi-axial measuring system adapted to detect a signal indicative of a motor state defined by a motion of a limb or of a plurality of parts of a body of the subject;
   a signal converter configured to convert the signal into data;
   a storage unit operatively coupled to the sensor and configured to receive and store the data detected by the multi-axial measurement system;
   a processor programmed to process and re-arrange the data stored in the storage unit according to processing operations, the processing operations comprising:
   processing the data by subdividing a recording sequence, during which the signal is collected, into time sub-intervals and by computing parameters for each sub-interval, the parameters comprising:
       a Fourier transform at each axis of the multi-axial measurement system, wherein a spectral processing determines a frequency content of the signal at each axis of the multi-axial measurement system,
       a motor activity parameter and a first integral of a power spectral density calculated by considering an entire frequency range,
       a second integral of the power spectral density calculated by considering a pre-determined frequency interval, and
       a ratio between the second integral and the first integral, wherein the ratio is adjusted to take into account whether, within each time sub-interval, a pronation-supination movement is determined, and whether the pronation-supination movement from the motion of the limb or of the plurality of parts matches a pronation-supination reference pattern to a predetermined degree;
   processing the parameters determined for each time sub-interval and computing an average value of the motor activity parameter by considering multiple time sub-intervals and an average value of the adjusted ratios between the second integral and the first integral over the multiple time sub-intervals; and
   comparing the parameters against a reference value or range, to verify whether the determined motor state matches a reference motor state to a predetermined degree;
   further comprising a user interface configured to interact with the processor, the user interface providing final results derived from the computed parameters using textual and/or graphical elements.

2. The system according to claim 1, wherein the multi-axial measuring system is a tri-axial accelerometer.

3. The system according to claim 1, wherein the determined motor state is matching the reference motor state when:

$$\begin{cases} a_{RMS} < a_T \\ BL > BL_T \end{cases}$$

wherein:
a_T and BL_T are thresholds,
$a_{RMS}$ is an average value of a root mean square acceleration values determined during the recording sequence,
BL is an average value of values of ratio between,
   (a) the second integral of the power spectral density calculated on the pre-determined frequency interval which is greater than zero for the time sub-intervals where the pronation-supination movement is determined, the second integral being equal to zero for the time sub-intervals where the pronation-supination movement is not determined, and
   (b) the first integral of the power spectral density calculated over an entire frequency range,
   determined during the recording sequence.

4. The system according to claim 1, wherein the processor is programmed to identify the motor state associated with Parkinson's disease tremor by considering the power spectral density and the frequency values within intervals between 3 and 7 Hz.

5. The system according to claim 1, wherein the processor is further programmed to perform:
   a computation of acceleration signals detected by the sensor to determine an average value of a root mean square acceleration determined during the active recording sequence,
   a spectral processing of the acceleration signals and a computation of the Fourier transform at each axis of the multi-axial measurement system, wherein the spectral processing determines the frequency content of the acceleration signals at each axis of the multi-axial measurement system, to determine one or more of:
   frequency peaks occurring in a specific frequency range, or
   one or more of the parameters related to Fourier transforms, and a comparison of one or more of the frequency peaks or the one or more of the parameters against reference values or ranges, to verify whether the determined motor state matches the reference motor state to the predetermined degree.

6. The system according to the claim 5, wherein the processor is further programmed:

to receive the signals detected during an execution of motor tests performed with the subject's hands and determine the motor state based on rest tremor amplitude and the pronation-supination movements of the hands, and, to verify whether the determined motor state matches the reference motor state if:

$$\begin{cases} a_{RMS} < a_{T,B} \\ f_{P,z} < f_{P,B} \end{cases}$$

during the recording session of the pronation-supination movements, and $$\begin{cases} a_{RMS} > a_{T,T} \\ f_{P,TL} \le f_{P,y} \le f_{P,TH} \end{cases}$$

during the recording session of the rest tremor amplitude, wherein:

$a_{T,T}$ and $a_{T,B}$ are thresholds, $f_{P,B}$, $f_{P,TL}$ and $f_{P,TH}$ are frequency values, $f_{P,z}$ is a frequency value in which a peak of the Fourier transform of an acceleration signal at a z-axis occurs during the recording session of the pronation-supination movements, $f_{P,y}$ is a frequency value in which the peak of the Fourier transform of an acceleration signal at a y-axis occurs during the recording session of the rest tremor amplitude.

7. The system according to the claim 5, wherein the processor is further programmed:

to receive the signals detected during an execution of motor tests performed with the subject's hands and determine a motor state based on rest tremor amplitude and the pronation-supination movements of the hands, and, to verify whether the determined motor state matches the reference motor state if:

$$\begin{cases} a_{RMS} < a_{T,B} \\ f_{P,z} < f_{P,B} \end{cases}$$

during the recording session of the pronation-supination movements, and $$A_{AVG} > A_{AVG,T}$$

during the recording session of the rest tremor amplitude, wherein:

$a_{T,T}$ and $A_{AVG,T}$ are thresholds, $f_{P,B}$, is a threshold frequency value, $f_{P,z}$ is a frequency value in which a peak of the Fourier transform of an acceleration signal at a z-axis occurs during the recording session of the pronation-supination movements, $A_{AVG}$ is the average value of values of the Fourier transforms $A_x$, $A_y$, $A_z$, in a range between 3 Hz and 7 Hz.

8. The system according to claim 1, wherein the processor is programmed to carry out a recording session over a single sub-interval.

9. The system according to claim 1, wherein the wearable device is configured to be worn on a wrist of the subject.

10. The system according to claim 1, further comprising an external processing unit in communication with the wearable device and housing the processor.

11. A method of use of a system configured to determine a motor state of a patient, the method comprising:

providing a system according to claim 1;

causing the subject to wear the wearable device;

causing the processor to perform the processing operations;

causing the user interface to provide the final results derived from the computed parameters using textual and/or graphical elements.

12. The method according to claim 11, wherein causing the processor to perform the processing operations comprises causing the processor to carry out a recording session continuously over a predetermined amount of time and passively, without involvement by the subject in pre-determined motor tasks.

13. The method according to claim 11, wherein causing the processor to perform the processing operations comprises causing the processor to carry out a recording session continuously over a predetermined amount of time and actively, with an active involvement of the subject in predetermined motor tasks.

14. The system method to claim 13, wherein causing the processor to perform the processing operations comprises causing the processor to perform, during a recording sequence in which the subject is actively involved in predetermined motor tasks:

a computation of acceleration signals detected by the sensor to determine an average value of a root mean square acceleration determined during the active recording sequence, a spectral processing of the acceleration signals and a computation of the Fourier transform at each axis of the multi-axial measurement system, wherein the spectral processing determines the frequency content of the acceleration signals at each axis of the multi-axial measurement system, to determine one or more of:

frequency peaks occurring in a specific frequency range, or one or more of the parameters related to Fourier transforms, and a comparison of one or more of the frequency peaks or the one or more of the parameters against reference values or ranges, to verify whether the determined motor state matches the reference motor state to the predetermined degree.

15. The method according to the claim 13, wherein the processor is further programmed:

to receive the signals detected during an execution of motor tests performed with the subject's hands and determine the motor state based on rest tremor amplitude and the pronation-supination movements of the hands, and, to verify whether the determined motor state matches the reference motor state if:

$$\begin{cases} a_{RMS} < a_{T,B} \\ f_{P,z} < f_{P,B} \end{cases}$$

during the recording session of the pronation-supination movements, and $$\begin{cases} a_{RMS} > a_{T,T} \\ f_{P,TL} \le f_{P,y} \le f_{P,TH} \end{cases}$$

during the recording session of the rest tremor amplitude, wherein:

$a_{T,T}$ and $a_{T,B}$ are thresholds, $f_{P,B}$, $f_{P,TL}$ and $f_{P,TH}$ are frequency values, $f_{P,z}$ is a frequency value in which a peak of the Fourier transform of an acceleration signal at a z-axis occurs during the recording session of the pronation-supination movements, $f_{P,y}$ is a frequency value in which the peak of the Fourier transform of an acceleration signal at a y-axis occurs during the recording session of the rest tremor amplitude.

16. The method according to the claim 13, wherein the processor is further programmed:

to receive the signals detected during an execution of motor tests performed with the subject's hands and determine a motor state based on rest tremor amplitude and the pronation-supination movements of the hands, and, to verify whether the determined motor state matches the reference motor state if:

$$\begin{cases} a_{RMS} < a_{T,B} \\ f_{P,z} < f_{P,B} \end{cases}$$

during the recording session of the pronation-supination movements, and $$A_{AVG} > A_{AVG,T}$$

during the recording session of the rest tremor amplitude, wherein:

$A_{T,T}$ and $A_{AVG,T}$ are thresholds, $f_{P,B}$, is a threshold frequency value, $f_{P,z}$ is a frequency value in which a peak of the Fourier transform of an acceleration signal at a z-axis occurs during the recording session of the pronation-supination movements, $A_{AVG}$ is the average value of values of the Fourier transforms $A_x$, $A_y$, $A_z$, in a range between 3 Hz and 7 Hz.

17. The method according to claim 11, wherein causing the processor to perform the processing operations comprises causing the processor to carry out a recording session the recording sequence continuously over a predetermined amount of time and with an active involvement of the subject in pre-determined motor tasks.

18. The method according to claim 11, wherein causing the processor to perform the processing operations comprises causing the processor to carry out recording sessions actively, with an active involvement of the subject, and passively, without involvement by the subject in pre-determined motor tasks.

19. The method according to claim 15, wherein the processor is further programmed to confirm results obtained passively during the recording sessions with results obtained actively during the recording session.

* * * * *